US008001962B2

(12) United States Patent
Sheiman

(10) Patent No.: US 8,001,962 B2
(45) Date of Patent: Aug. 23, 2011

(54) NEBULIZING AND DRUG DELIVERY DEVICE

(75) Inventor: Vladimir Sheiman, Sydney (AU)

(73) Assignee: Sheiman Ultrasonic Research Foundation Pty Ltd., Sydney, New South Wales (AU)

(*) Notice: Subject to any disclaimer, the term of this patent is extended or adjusted under 35 U.S.C. 154(b) by 1093 days.

(21) Appl. No.: 10/525,373

(22) PCT Filed: Aug. 23, 2003

(86) PCT No.: PCT/AU03/01079

§ 371 (c)(1), (2), (4) Date: Feb. 23, 2005

(87) PCT Pub. No.: WO2004/017848
PCT Pub. Date: Mar. 4, 2004

(65) Prior Publication Data
US 2006/0137680 A1 Jun. 29, 2006

(30) Foreign Application Priority Data

Aug. 23, 2002 (AU) ................................ 2002950965
Dec. 2, 2002 (AU) ................................ 2002953039

(51) Int. Cl.
*A61M 11/00* (2006.01)
*A61M 15/00* (2006.01)
(52) U.S. Cl. ......... 128/200.14; 128/200.16; 128/200.18; 239/338; 239/370; 239/102.1; 239/102.2
(58) Field of Classification Search ............. 128/200.14, 128/200.16, 200.18; 239/338, 370, 102.1, 239/102.2
See application file for complete search history.

(56) References Cited

U.S. PATENT DOCUMENTS 2,027,298 A 1/1936 Wheat
2,228,009 A 1/1941 Harford (Continued)

FOREIGN PATENT DOCUMENTS

CN 1143528 8/1995
(Continued)

OTHER PUBLICATIONS

Khmelev et al., RU 2070062C1, Dec. 10, 1996, English translation provided by The McElroy Translation Company, PTO 09-2827, entire document.*

*Primary Examiner* — Justine R Yu
*Assistant Examiner* — Clinton Ostrup
(74) *Attorney, Agent, or Firm* — Miles & Stockbridge P.C.

(57) ABSTRACT

The invention relates generally to a nebulizer, for example, of ultrasonic nebulizer (30) having a bowl shaped container (12) and a tubular energy transmitter in the form of acoustic transmitter pipe (34). One end of the acoustic transmitter pipe (34) is immersed in the liquid (14) of the container (12). The bowl shaped ultrasonic transducer (16) is operatively coupled to the bowl shaped container (12) for transmission of ultrasonic energy to the liquid (14) and acoustic transmitter pipe (34). Absorption of transmitted energy by the liquid (14) forces the liquid (14) toward an upper end of the acoustic transmitter pipe (34) where it is nebulized in the form of an aerosol. The invention also relates generally to a device and method for delivering a substance in an aerosol form into a cellular organism, and a hand held device for delivering a substance to a cellular organism.

21 Claims, 1 Drawing Sheet

U.S. PATENT DOCUMENTS

| | | | |
|---|---|---|---|
| 2,659,042 A | 11/1953 | Anderson et al. | |
| 3,169,524 A | 2/1965 | Langevin | |
| 3,274,476 A | 9/1966 | Wildum | |
| 3,387,607 A | 6/1968 | Gauthier et al. | |
| 3,433,461 A | 3/1969 | Scarpa | |
| 3,472,455 A | 10/1969 | Johnson et al. | |
| 3,490,697 A | 1/1970 | Best, Jr. | |
| 3,806,100 A | 4/1974 | Cornett et al. | |
| 3,828,201 A | 8/1974 | Allen, Sr. | |
| 3,918,641 A | 11/1975 | Lehmann et al. | |
| 3,919,615 A | 11/1975 | Niecke | |
| 4,007,238 A | 2/1977 | Glenn | |
| 4,094,317 A | 6/1978 | Wasnich | |
| 4,113,809 A | 9/1978 | Abair et al. | |
| 4,200,093 A | 4/1980 | Camp | |
| 4,244,361 A | 1/1981 | Neubert | |
| 4,410,139 A * | 10/1983 | Nishikawa et al. | 239/102.2 |
| 4,656,707 A | 4/1987 | Berte et al. | |
| 4,667,141 A | 5/1987 | Steele | |
| 4,714,078 A | 12/1987 | Paluch | |
| 4,792,097 A | 12/1988 | Kremer et al. | |
| 4,820,453 A | 4/1989 | Huang | |
| 4,902,955 A | 2/1990 | Manis et al. | |
| 4,951,661 A | 8/1990 | Sladek | |
| 4,961,885 A * | 10/1990 | Avrahami et al. | 261/142 |
| 4,976,259 A | 12/1990 | Higson et al. | |
| 5,062,419 A | 11/1991 | Rider | |
| 5,209,225 A | 5/1993 | Glenn | |
| 5,214,368 A | 5/1993 | Wells | |
| 5,226,411 A | 7/1993 | Levine | |
| 5,241,954 A | 9/1993 | Glenn | |
| 5,277,175 A | 1/1994 | Riggs et al. | |
| 5,308,180 A | 5/1994 | Pournoor et al. | |
| 5,361,989 A | 11/1994 | Merchat et al. | |
| 5,429,302 A | 7/1995 | Abbott | |
| 5,464,386 A | 11/1995 | Hofmann | |
| 5,474,059 A | 12/1995 | Cooper | |
| 5,485,827 A | 1/1996 | Zapol et al. | |
| 5,646,470 A | 7/1997 | de Groot | |
| 5,687,715 A | 11/1997 | Landis et al. | |
| 5,707,352 A | 1/1998 | Sekins et al. | |
| 5,724,965 A | 3/1998 | Handke et al. | |
| 5,741,317 A | 4/1998 | Ostrow | |
| 5,756,994 A | 5/1998 | Bajic | |
| 5,829,434 A | 11/1998 | Ambrosio et al. | |
| 5,865,171 A | 2/1999 | Cinquin | |
| 5,908,158 A | 6/1999 | Cheiman | |
| 5,921,232 A | 7/1999 | Yokoi et al. | |
| 5,983,134 A | 11/1999 | Ostrow | |
| 6,007,940 A | 12/1999 | Spotnitz | |
| 6,041,253 A | 3/2000 | Kost et al. | |
| 6,106,971 A | 8/2000 | Spotnitz | |
| 6,152,383 A | 11/2000 | Chen | |
| 6,202,642 B1 | 3/2001 | McKinnon et al. | |
| 6,234,167 B1 | 5/2001 | Cox et al. | |
| 6,237,589 B1 | 5/2001 | Denyer et al. | |
| 6,241,162 B1 | 6/2001 | Takahashi | |
| 6,283,118 B1 | 9/2001 | Lu | |
| 6,328,030 B1 | 12/2001 | Kidwell et al. | |
| 6,357,671 B1 | 3/2002 | Cewers | |
| 6,379,616 B1 * | 4/2002 | Sheiman | 422/31 |
| 6,402,046 B1 | 6/2002 | Löser | |
| 6,443,146 B1 | 9/2002 | Voges | |
| 6,478,754 B1 * | 11/2002 | Babaev | 601/2 |
| 6,490,186 B2 | 12/2002 | Cho | |
| 6,501,197 B1 | 12/2002 | Cornog et al. | |
| 6,516,802 B2 | 2/2003 | Hansen et al. | |
| 6,530,370 B1 | 3/2003 | Heinonen | |
| 6,530,570 B2 | 3/2003 | Ku | |
| 6,550,476 B1 | 4/2003 | Ryder | |
| 6,640,804 B2 | 4/2003 | Ivri et al. | |
| 6,628,798 B2 | 9/2003 | Teshima et al. | |
| 6,725,858 B2 | 4/2004 | Loescher | |
| 6,727,446 B1 | 4/2004 | Mayo et al. | |
| 6,851,427 B1 | 2/2005 | Nashed | |
| 6,854,465 B2 | 2/2005 | Bordewick et al. | |
| 7,037,306 B2 | 2/2006 | Podany | |
| 7,059,320 B2 | 6/2006 | Feiner et al. | |
| 7,080,643 B2 | 7/2006 | Grychowski et al. | |
| 7,089,941 B2 | 8/2006 | Bordewick et al. | |
| 7,179,254 B2 | 2/2007 | Pendekanti | |
| 7,211,320 B1 | 5/2007 | Cooper | |
| 2002/0007869 A1 * | 1/2002 | Pui et al. | 141/173 |
| 2002/0011248 A1 | 1/2002 | Hansen et al. | |
| 2002/0082666 A1 * | 6/2002 | Babaev | 607/89 |
| 2003/0136407 A1 * | 7/2003 | Matsuyama | 128/203.16 |
| 2003/0140921 A1 | 7/2003 | Smith et al. | |
| 2003/0196660 A1 | 10/2003 | Haveri | |
| 2003/0205229 A1 | 11/2003 | Crockford et al. | |
| 2004/0025882 A1 | 2/2004 | Madaus et al. | |
| 2004/0119415 A1 | 6/2004 | Lansing et al. | |
| 2004/0267167 A1 | 12/2004 | Podany | |
| 2005/0010202 A1 | 1/2005 | Podany | |
| 2005/0042170 A1 | 2/2005 | Jiang et al. | |
| 2005/0215942 A1 | 9/2005 | Abrahamson | |
| 2006/0151624 A1 | 7/2006 | Grundler et al. | |
| 2006/0163641 A1 | 7/2006 | Okumura | |
| 2006/0201500 A1 | 9/2006 | Von Hollen | |
| 2006/0201501 A1 | 9/2006 | Van Hollen | |
| 2006/0201502 A1 | 9/2006 | Lieberman et al. | |
| 2006/0243274 A1 | 11/2006 | Lieberman et al. | |
| 2007/0277816 A1 | 12/2007 | Morrison et al. | |

FOREIGN PATENT DOCUMENTS

| | | |
|---|---|---|
| RU | 2070062 | 12/1996 |
| RU | 2070062 C1 * | 12/1996 |
| RU | 2076746 | 4/1997 |
| WO | WO 95/26236 | 10/1995 |
| WO | WO 9942145 A1 * | 8/1999 |
| WO | WO 00/23144 A1 | 4/2000 |
| WO | WO 03/035152 | 5/2003 |

* cited by examiner

NEBULIZING AND DRUG DELIVERY DEVICE

FIELD OF THE INVENTION

The present invention relates broadly to a nebulizer, and in particular an ultrasonic nebulizer, as well as a method and a device for delivering a substance in an aerosol form into a cellular organism. The invention also relates generally to a handheld device for delivering a substance to a cellular organism. The invention relates particularly, though not exclusively, to nebulization of drugs and radiation or energy assisted delivery of aerosol and non aerosol forms of drugs to cellular organisms.

BACKGROUND OF THE INVENTION

Drugs are commonly administered orally by absorption through a patient's digestive tract. This method of drug administration involves systemic delivery of high doses of a drug which results in only a small percentage of the drug reaching a target area. Because of the high dosage, toxic side effects are often involved. In order, to address these problems alternative forms of drug delivery are being used for an increasing number of applications. The alternative forms of drug delivery typically involve: (i) inhalation, and (ii) trans skin or transdermal transport which is technically known as transdermal drug delivery.

Drug delivery via inhalation can involve an aerosol form of a drug. Aerosol forms of a drug are usually provided by atomization of a liquid solution form of the drug to form aerosol, immediately prior to drug delivery. Atomization is typically most efficiently effected by nebulization of a liquid, usually but not exclusively, with an ultrasonic nebulizer.

Ultrasonic nebulizers typically include an ultrasonic transducer which is positioned below a liquid filled container. For example, in more efficient nebulizers the ultrasonic transducer is designed to focus ultrasonic radiation to a specific point within the container. The focussed radiation results in formation of an upwardly projecting fountain of liquid and the formation of aerosol droplets at the fountain. Ultrasonic nebulizers operate efficiently when the liquid surface passes through the focal point of the ultrasonic transducer. However, they operate poorly or not at all if the liquid surface is above or below the ultrasonic transducer focal point. Conversion of liquid to aerosol causes the liquid surface to lower which in turn adversely affects a nebulizer's efficiency.

Transdermal drug delivery can involve passive diffusion and active transport. Passive diffusion of a drug through the skin is the diffusion that occurs naturally when small-molecule drugs are applied to the skin in sufficient concentration and for a sufficient period of time to enable natural diffusion through the skin. However, passive diffusion is slow and furthermore, because of the skin's natural barriers to passage of externally applied substances, passive diffusion is not suitable for most drugs. Active transdermal drug delivery techniques include sonophoresis, iontophoresis, electroporation and magnetophoresis. Sonophoresis involves the application of ultrasound, iontophoresis and electroporation involve the application of an electric field and magnetophoresis involves the application of a magnetic field.

U.S. Pat. No. 5,741,317 discloses an apparatus which includes a therapy and drug treatment tub for submersion of a treatment area of a patient in a medicated solution. The tub includes acoustic transducers and rows of electrodes and coils for delivery of respective ultrasonic, electric and magnetic radiation to the patient. The radiation facilitates active transdermal drug delivery involving phonophoretic, iontophoretic and electromagnetophoretic transport mechanisms. However, the apparatus is very large and expensive and cannot readily be used for transdermal drug delivery to a specific region of a patient.

U.S. Pat. No. 5,983,134 discloses a flexible cuff connected to a liquid drug reservoir. The cuff is designed for attachment to a patient by wrapping around part of the patient's body to form an attached sleeve. Referring to FIG. 1 of U.S. Pat. No. 5,983,134, the attached sleeve can be elongate and encircle most of a patient's leg, or squat and encircles a patient's neck. The cuff is designed to transmit electric and magnetic fields to assist transdermal delivery of drugs provided at an internal cylindrical surface of the attached sleeve. While the cuff of U.S. Pat. No. 5,983,134 is suitable for transdermal drug delivery to a specific part of a patient's body, it is cumbersome to use and is only suitable for delivery of a drug to a circumferential segment of a patient's limb, torso or neck.

U.S. Pat. No. 5,464,386 discloses a transdermal drug delivery applicator which is designed to supply a fluid medium carrying drug loaded vesicles to a patient's skin via a curved head assembly. The applicator generates a pulsed electrical field to facilitate active transdermal transport mechanisms of electroporation and iontophoresis. The applicator is capable of providing active transdermal drug delivery to a specific part of a patient's body. However, the applicator is only able to provide active transdermal drug delivery involving electric radiation.

SUMMARY OF THE INVENTION

According to one aspect of the present invention there is provided a method of delivering a substance into a cellular organism, the method comprising the steps of:
  providing the substance in an ionized aerosol form at a delivery region of the organism; and
  applying magnetic energy to the delivery region to effect enhanced delivery of the ionized aerosol substance to the cellular organism.

Preferably the application of magnetic energy is effected by applying a pulsed magnetic field. More preferably the pulse magnetic field is asymmetric.

According to another aspect of the invention there is provided a method of delivering a substance into a cellular organism, the method comprising the steps of:
  providing the substance in a liquid or cream form at a delivery region of the organism;
  applying ultrasonic energy to the delivery region to enhance delivery of the cream or liquid substance to said organism; and
  simultaneously applying magnetic energy and electrical energy to the delivery region to effect delivery of the cream or liquid substance to the cellular organism.

Preferably the application of ultrasonic energy to said organism to enhance delivery is promoted by opening of pores of the organism.

Preferably the ultrasonic and magnetic energies are applied simultaneously.

Preferably the application of magnetic energy is effected by applying magnetic fields, the magnetic field is a pulsed magnetic field.

According to a further aspect of the invention there is provided a device for delivering a substance into a cellular organism, the device comprising:
  an aerosol delivery head for providing the substance in an ionized aerosol form at a delivery region of the organism;

means for applying magnetic energy to the delivery region to effect enhanced delivery of the ionized aerosol substance to the cellular organism.

Preferably the aerosol delivery head provides a sealed compartment about the delivery region.

Preferably the device further comprises a nebulizer being operatively coupled to the aerosol delivery head. More preferably the nebulizer comprises:

a container being adapted to contain a liquid to be nebulized;

a tubular energy transmitter having one end immersed in the liquid of the container and an opposite end positioned clear of the liquid; and an energy source being operatively coupled to the container or the tubular energy transmitter for nebulisation of the liquid and being arranged for transmission of the energy to the liquid or tubular energy transmitter whereby in operation the transmitted energy forces the liquid toward the opposite end of the tubular energy transmitter where it is nebulized in the form of the aerosol.

Preferably at least one energy transmitter is positioned so that said one end is adjacent the bottom of the liquid.

Preferably the energy transmitter is arranged to allow formation of high frequency vibrations in its wall(s) upon emission of the energy, the high frequency vibrations effecting aerosol formation at the liquid surface at or adjacent the opposite end of the energy transmitter.

Preferably the nebulizer further comprises an aerosol tube coupled to the opposite end of the tubular energy transmitter and having a cross-sectional area such that the static pressure of the aerosol within the aerosol tube induces a pressure drop along the aerosol tube which alone is sufficient to propel the nebulized aerosol through the aerosol tube.

According to yet another aspect of the invention there is provided a device for delivering a substance into a cellular organism, the device comprising:

means for generating ultrasonic energy being adapted to cooperate with a delivery region of the organism to enhance delivery of the substance in a cream or liquid form to said organism;

means for simultaneously applying magnetic energy and electrical energy to the delivery region to effect delivery of the cream or liquid substance to the cellular organism, said ultrasonic generating means being operatively coupled to the magnetic and electrical energy means whereby a synergistic effect is provided by the combination of said means.

Preferably the means for applying magnetic energy is in the form of a pulsed magnetic generator.

The organism of the various aspects of the present invention may be an animal. More particularly, the organism may be a human being. The delivery region may comprise a membrane of the animal or human being. The membrane may comprise skin of the human being. Alternatively, the membrane may comprise a cornea of the human being. The membrane may alternatively comprise a lung of the human being.

According to another aspect of the invention there is a nebulizer comprising:

a container adapted to contact a liquid to be nebulized;

a tubular energy transmitter having one end proximate the container; and an energy source being operatively coupled to the container for nebulisation of the liquid and being arranged for transmission of energy to the liquid which is forced toward an opposite end of the tubular energy transmitter.

Preferably the energy source is positioned below the container.

a container adapted to contain a liquid to be nebulized;

a tubular energy transmitter including an acoustic transmitter pipe having one end immersed in the liquid proximate and spaced from the container;

an aerosol tube positioned around a portion of the acoustic transmitter pipe;

an acoustic energy source being operatively coupled to the container for nebulization of the liquid and being configured for transmission of acoustic energy to a focal region of the liquid proximate said one end of the acoustic transmitter pipe whereby said liquid is forced toward an opposite end of the acoustic transmitter pipe where a guided spout of said liquid is emitted with a diameter equal to a diameter of said opposite end of said acoustic transmitter pipe, the guided spout nebulized within the aerosol tube.

Preferably the energy source is positioned below the container.

Preferably said one end of the tubular energy transmitter is immersed in the liquid. Even more preferably the tubular energy transmitter is positioned so that said one end is proximate the bottom of the container. Even still more preferably the tubular energy transmitter vibrates at a frequency to form an aerosol proximate the opposite end of the energy transmitter.

Preferably the nebulizer further comprises an aerosol tube positioned about at least a portion of the tubular energy transmitter and having a cross-sectional area such that the pressure of the aerosol within the aerosol tube induces a pressure drop along the aerosol tube which propels the aerosol through the aerosol tube. Even more preferably an internal diameter of the aerosol tube is greater than an internal diameter of the tubular energy transmitter at its opposite end. Still more preferably the aerosol tube is positioned so that it is substantially coaxial with the tubular energy transmitter. Even still more preferably the aerosol tube is connected to the opposite end of the tubular energy transmitter.

Preferably the energy source vibrates the liquid proximate the opposite end of the tubular energy transmitter.

Preferably the aerosol tube opens at its upper end into an expansion chamber which in turn communicates with an outlet duct.

Preferably the expansion chamber is adapted to recirculate larger drops of the liquid back into the container.

Preferably the energy source comprises an ultrasonic transducer for transmission of ultrasonic radiation energy. Preferably the ultrasonic transducer has a concave shaped surface. Still more preferably the ultrasonic transducer is arranged to transmit ultrasonic energy to a focal region of the liquid.

Preferably said the one end of the tubular energy transmitter is proximate the focal region. More preferably an internal diameter of the tubular energy transmitter is substantially equal to a diameter of the focal region. Still more preferably the tubular energy transmitter has a higher acoustic impedance than the liquid. Even still more preferably the acoustic impedance of the tubular energy transmitter is high enough to effect minimal acoustic energy loss during transmittal of the energy along the tubular energy transmitter.

Preferably the application of ultrasonic energy is effected by applying ultrasonic fields.

Preferably the application of electrical energy is effected by applying ultrasonic fields.

BRIEF DESCRIPTION OF THE DRAWINGS

A preferred embodiment of the present invention will now be described, by way of example only, with reference to the accompanying drawings, in which.

DETAILED DESCRIPTION OF THE PREFERRED EMBODIMENT

Figure 1:
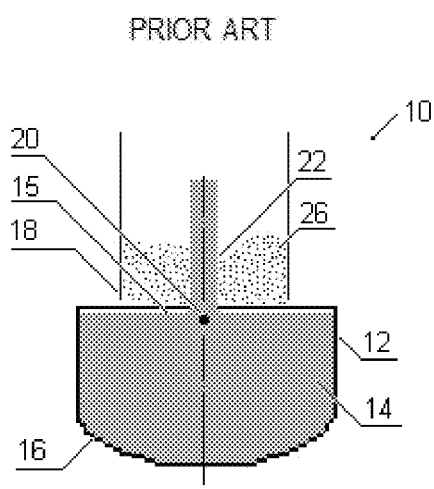
FIG. 1 is a schematic side elevational view of part of an ultrasonic nebulizer disclosed in the applicant's U.S. patent

U.S. Pat. No. 5,908,158 discloses the applicant's ultrasonic nebulizers which are predecessors to the preferred form of nebulizer of the present invention. The contents of U.S. Pat. No. 5,908,158 are hereby incorporated into this specification. FIG. 1 is a schematic representation of the nebulizer of U.S. Pat. No. 5,908,158. The nebulizer 10 includes a container in the form of bowl shaped container 12 which contains liquid 14, an energy source in the form of bowl shaped ultrasonic transducer 16 and an aerosol tube 18. The bowl shaped ultrasonic transducer 16 is designed to focus emitted ultrasonic radiation energy at an acoustic focal region, in this example acoustic focal point 20, which is located just beneath an upper surface of the liquid 14. Energy absorbed at the acoustic focal point 20 by the liquid 14 causes liquid to project upwardly to form a liquid spout 22.

In addition to formation of the liquid spout 22, ultrasonic radiation focussed at the acoustic focal point 20 results in transmission of acoustic energy upwardly through the liquid spout 22. When the acoustic energy reaches an upper surface of the liquid spout 22 it results in nebulization of liquid molecules which form at the upper surface and the subsequent formation of aerosol 26. Aerosol formation is understood to occur by a process which most likely involves capillary wave and cavitation mechanisms involving high frequency vibrations.

The liquid 14 can be a liquid or liquid suspension form of any substance which is required in an aerosol form. For example, the liquid 14 could include a medicated substance, for example a drug, or alternatively could be a perfume. The aerosol 26 is a vaporised form of the liquid 14 and can be administered to a cellular organism which for the purpose of this example is a person or patient. The aerosol 26 can be administered to a patient, for example, by inhalation or transferal through external cells of a patient's body such as those comprising their skin or cornea.

The aerosol 26 is administered to a patient by propelling it upwardly through the aerosol tube 18 which corresponds to the intake tube of the applicant's U.S. Pat. No. 5,908,158. Aerosol 26 formed from the nebulizer can be administered to a patient by placing a delivery region, which in this example is a patient treatment site or specific part of a patient's body, near the aerosol 26 and allowing the aerosol 26 to be administered to the patient treatment site by diffusion.

As the liquid 14 is nebulized by the nebulizer 10 and aerosol 26 is formed above the liquid 14, this nebulization of the substance results in depletion of the volume of liquid 14 which is contained by the bowl shaped container 12. As the volume of liquid 14 decreases the upper surface 15 of the liquid 14 moves downwardly. Once the upper surface 15 moves below the acoustic focal point 20 the rate of conversion of liquid 14 to aerosol 26 dramatically reduces to cause a corresponding reduction in efficiency of operation of the nebulizer 10.

Figure 2:
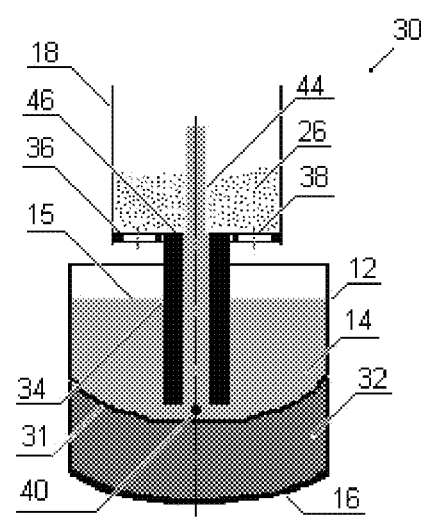
FIG. 2 is a schematic side elevational view of part of one example of an ultrasonic nebulizer of the present invention which has an ultrasonic transducer positioned beneath liquid which is contained in the nebulizer.

FIG. 2 shows one example of an ultrasonic nebulizer 30 of the present invention. For ease of reference like features of this ultrasonic nebulizer 30 and the previously described nebulizer 10 are referenced by common reference numerals. The ultrasonic nebulizer 30 includes a bowl shaped container 12 which contains liquid 14 having an upper surface 15, a bowl shaped ultrasonic transducer 16 and an aerosol tube 18. The ultrasonic nebulizer 30 also includes ultrasonic transmission medium 32 in the form of water which is positioned between the bowl shaped ultrasonic transducer 16 and the bottom of the bowl shaped container 12. The separation of the transmission medium from the nebulized liquid is made with a separator 31 which extends across the container 12. The nebulizer 30 also includes a tubular energy transmitter in the form of an acoustic transmitter pipe 34 which is supported by the aerosol tube 18 via a connection plate which in this example is an annular disc 36. The acoustic transmitter pipe 34 is cylindrical in shape however the tubular energy transmitter is not limited to this shape. For example, in an alternative form the tubular energy transmitter is a bell-shaped pipe (not shown). The transmitter pipe 34 and the aerosol tube 18 are arranged coaxial with one another. The annular disc 36 includes connection plate apertures in the form of holes 38. The bowl shaped ultrasonic transducer 16 focuses ultrasonic radiation at acoustic focal point 40 which is just above the bottom of the liquid 14 but below one end of the acoustic transmitter pipe 34 which in this particular example is a lower end 42. The correct focal point is achieved by appropriately designing the radius of curvature of the bowl shaped ultrasonic transducer 16 and the spacing between it and a bottom of the bowl shaped container 12.

Absorption of ultrasonic radiation energy by liquid 14 at the acoustic focal point 40 forces liquid upwardly through the acoustic transmitter pipe 34 to form a guided liquid spout 44. The guided liquid spout 44 extends beyond an upper surface of the acoustic transmitter pipe 34 and the annular disc 36 as shown in FIG. 2. Energy imparted to the liquid 14 at the acoustic focal point 40 results in transmission of acoustic energy upwardly through the guided liquid spout 44 and the wall of the acoustic transmitter pipe 34. Aerosol 26 is produced at the exit of the acoustic transmitter pipe 34. The kinetic energy of the aerosol 26 derived from the spout 44 induces a pressure drop along the aerosol tube 18 which propels the aerosol through the tube 18. The acoustic energy also transmits to the annular disc 36. The presence of acoustic energy at an upper surface 46 of the acoustic transmitter pipe 34, upper surface 48 of the annular disc 36 and upper longitudinal and lateral surfaces 50 and 52 respectively of the guided liquid spout 44, result in the formation of aerosol at those surfaces. In addition to supporting the acoustic transmitter pipe 34 the annular disc 36 increases the rate of which liquid 14 is converted to aerosol 26. Delivery of aerosol 26 formed by the ultrasonic nebulizer 30 to a patient treatment site (not shown) is as explained above in relation to the nebulizer 10. The acoustic impedance of the acoustic transmitter pipe 34 is higher than that of the liquid 14 to prevent radiation dispersing from the acoustic transmitter pipe 34 during transmittal along it. The acoustic impedance is high enough to effect minimal acoustic energy loss during transmission of the ultrasonic radiation.

Figure 3:
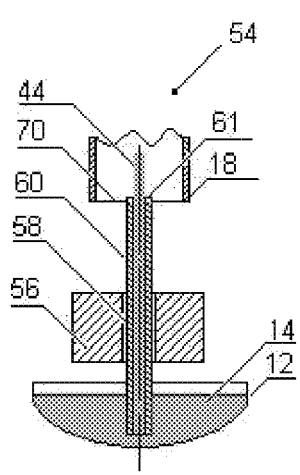
FIG. 3 is a schematic side elevational view of part of another example of a nebulizer of the present invention having an ultrasonic transducer positioned above liquid contained in the ultrasonic nebulizer.

FIG. 3 shows an example of a radially spaced energy source in the form of an ultrasonic transducer 56 which encircles a longitudinal mid segment 58 of a tubular energy transmitter in the form of an acoustic transmitter pipe 60. The ultrasonic transducer 56 and acoustic transmitter pipe 60 can be substituted for the ultrasonic transducer 16, ultrasonic transmission medium 32 and acoustic transmitter pipe 34 of the ultrasonic nebulizer 30 to form ultrasonic nebulizer 54. The ultrasonic transducer 56 transmits ultrasonic radiation energy directly to the acoustic transmitter pipe 60 and the liquid 14. Ultrasonic radiation energy absorbed by the liquid 14 results in the liquid 14 being forced upwardly through the acoustic transmitter pipe 60 to form a guided liquid spout 44. The mechanism which is understood to be responsible for formation of the guided liquid spout 44 is known as the sonocapillary effect. Energy imparted to the acoustic transmitter pipe 60 is transmitted upwardly along walls of the acoustic transmitter pipe 60 as explained above in relation to the acoustic transmitter pipe 34. Liquid is nebulized as explained above in relation to the ultrasonic nebulizer 30 by interaction of the acoustic energy with the liquid spout and upper surfaces of the acoustic transmitter pipe 60.

The ultrasonic nebulizers 30 and 54 can include additional components described in relation to the ultrasonic nebulizer of U.S. Pat. No. 5,908,158. For example, the ultrasonic nebulizers 30 and 54 can include an expansion chamber, for example, expansion chamber 9 of nebulizers of U.S. Pat. No. 5,908,158 (see FIGS. 1, 2, 3, 4, 6 and 8) and an outlet duct. Examples of outlet ducts are ducts 11, 26 and 29 of FIGS. 1, 5 and 6 of U.S. Pat. No. 5,908,158. In ultrasonic nebulizers 30 and 54 which include an expansion chamber (not shown), the aerosol tube 18 functions as the intake tube 8 of U.S. Pat. No. 5,908,158 and can be supported relative to an expansion chamber in a similar manner to that which the intake tube 8 of U.S. Pat. No. 5,908,158 is supported relative to expansion chamber 9. An expansion chamber enables any un-nebulize drops of liquid which issue from the aerosol tube 18 to be recirculated back into the liquid 14 as described in U.S. Pat. No. 5,908,158, for subsequent nebulization. Ultrasonic nebulizers 30 and 54 which include an expansion chamber and an aerosol tube 18 which is free of the acoustic transmitter pipe 34 or 60 respectively, still include a flange at upper ends 35 and 61 of acoustic transmitter pipes 34 and 60 respectively which in this example corresponds to annular discs of 36 and 70 respectively.

The cross sectional area of the aerosol tube 18 of ultrasonic nebulizers 30 and 54 referred to above is such that the pressure of aerosol 26 within the aerosol tube 18 induces a pressure drop as aerosol 26 moves upwardly along the aerosol tube 18. This pressure drop propels aerosol 26 upwardly through the aerosol tube 18 avoiding the need for any independent means of propulsion, e.g., a fan. Correct cross sectional dimensions of the aerosol tube 18 ensure that aerosol 26 can be efficiently and effectively admitted to a patient treatment site (not shown).

Figure 4:
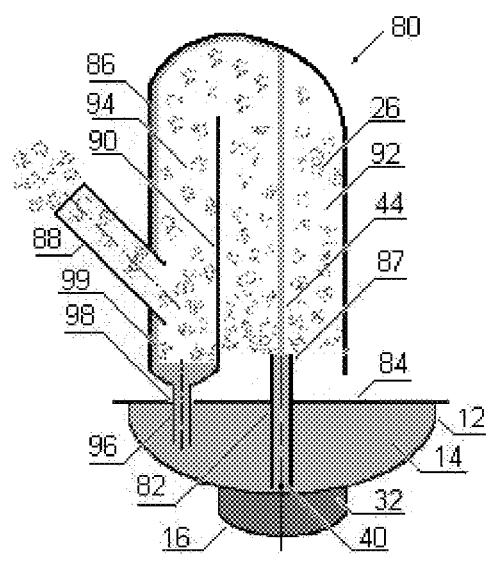
FIG. 4 is a schematic side elevational view of a third example of an ultrasonic nebulizer of the present invention.

Referring to FIG. 4, an ultrasonic nebulizer 80 is described using reference numerals of the nebulizer 10 of FIG. 1 and ultrasonic nebulizers 30 and 54 of FIGS. 2 and 3, respectively, to describe common features. The ultrasonic nebulizer 80 includes a bowl shaped container 12 which contains liquid 14, a bowl shaped ultrasonic transducer 16, ultrasonic transmission medium 32 for transmission of ultrasonic radiation emitted by the bowl shaped ultrasonic transducer 16 to the liquid 14. The ultrasonic nebulizer 80 also includes an acoustic transmitter pipe 82 which is similar to the acoustic transmitter pipe 34 of the ultrasonic nebulizer 30. The acoustic transmitter pipe 82 is supported relative to the bowl shaped container 12 by an annular support disc 84 which sits on top of the bowl shaped container 12 to enclose the container 12. Ultrasonic radiation emitted by the bowl shaped ultrasonic transducer 16 is focused to an acoustic focal point 40 as described above in relation to the ultrasonic nebulizer 30. Aerosol 26 is formed at an upper end 87 of the acoustic transmitter pipe 82 also as described above in relation to the ultrasonic nebulizer 30.

The ultrasonic nebulizer 80 differs from examples of ultrasonic nebulizers 30 and 54 described above in that it includes an expansion chamber which in this example is expansion chamber 86. Expansion chamber 86 includes an outlet duct in the form of outlet pipe 88. The outlet pipe 88 is partitioned from the acoustic transmitter pipe 82 by an upright partition wall 90 which is positioned to one side of the expansion chamber 86 to form a main compartment 92 which is positioned directly over the acoustic transmitter pipe 82 so that the acoustic transmitter pipe 82 is approximately aligned with an upright longitudinal axis of the main compartment 92. The partitioned wall 90 also forms a side compartment 94 which connects to a side compartment drain pipe 96 that extends downwardly through a hole 98 in the annular support disc 84 and into the liquid 14 of the bowl shaped container 12. The expansion chamber 86 is supported relative to the bowl shaped container 12 by the annular support disc 84. The partition wall 90 stops short of an upper inner surface of the expansion chamber 86 for movement of gas between the main and side compartments 92 and 94 respectively.

The cross sectional area of the main compartment 92 is such that aerosol 26 which is formed at the upper end 87 of the acoustic transmitter pipe 82 is propelled upwardly within the main compartment 92. When aerosol 26 moving upwardly within the main compartment 92 meets an upper inner surface of the expansion chamber 86 it is directed by that surface to flow over an upper end of the partition wall 90 and into an upper end of the side compartment 94. Because of the propulsion provided to the aerosol 26 as it moves upwardly within the main compartment 92, the aerosol 26 is forced downwardly into the side compartment 94. As the aerosol 26 flows in a downward direction it passes the outlet pipe 88 which provides a lower energy route than if the aerosol 26 were to continue downwardly beyond the outlet pipe 88. The aerosol 26 therefore exits the side compartment 94 via the outlet pipe 88 for administration to a patient treatment site (not shown).

Liquid 99 in the main compartment 92 and side compartment 94 can occur either by liquid being projected directly upwardly from the acoustic transmitter pipe 82 by virtue of ultrasonic energy applied to the liquid 14 at the acoustic focal point 40 or by condensation of aerosol 26 during circulation of aerosol 26 from the main compartment 92 to the side compartment 94. When the ultrasonic nebulizer 80 is optimally adjusted the liquid 99 includes a minimal un-nebulized component and therefore effectively only comprises condensed aerosol 26. Most of the condensed aerosol 26 circulates into the side compartment 94 for drainage down into the liquid 14 via the side compartment drain pipe 96.

Now that various examples of a preferred embodiment and method of delivering a substance into a cellular organism have been described, it will be apparent to those skilled in the art that the preferred embodiment and methodology have at least the following advantages:

(a) the efficiency and effectiveness of the nebulizer is maintained during nebulization unlike the prior art where the liquid level is progressively lowered with conversion of the liquid into aerosol;

(b) the device effectively provides an aerosol form of a substance at a delivery region of a cellular organism for delivery thereto;

(c) the application of an aerosol form of a substance to delivery regions of a cellular organism is possible where contact of the delivery regions by liquid or solid matter is adverse or sensitive;

(d) the delivery of an aerosol form of a substance into a cellular organism is possible through active transport techniques involving the application of one or more forms of radiation or energy;

(e) the delivery of an aerosol form of a substance into a cellular organism is possible through simultaneous application of two or more different forms of radiation or energy;

(f) the delivery of an aerosol form of a substance into a cellular organism is possible through simultaneous application of two or more different forms of radiation or energy in a synergistic manner whereby different form of radiation or energy collectively enhance delivery more than the sum of delivery enhancements achievable through independent application of the different forms of radiation or energy;

(g) the substance delivery can be confined to a relatively small part of a cellular organism by simultaneous application of two or more different forms of radiation via a radiation delivery head of a substance delivery gun; and (h) the delivery of a substance via a delivery gun through simultaneous application of two or more different forms of radiation or energy in a synergistic manner whereby different forms of radiation or energy collectively enhance delivery more than the sum of delivery enhancements achievable through independent application of the different forms of radiation or energy.

Those skilled in the art will appreciate that the invention described herein is susceptible to variations and modifications other than those specifically described. For example, the specific shape and design of the nebulizer, and the aerosol and substance delivery guns, as well as the specific shape, design or configuration of components or assemblies that they comprise may vary provided they function as broadly defined.

All such variations and modifications are to be considered within the scope of the present invention the nature of which is to be determined from the foregoing description.

It is to be understood that a reference herein to a prior art document does not constitute an admission that the document forms part of the common general knowledge in the art in Australia or in any other country.

The claims defining the invention are as follows:

1. A nebulizer comprising:
   a container adapted to contain a liquid to be nebulized;
   a tubular energy transmitter including an acoustic transmitter pipe having one end immersed in the liquid proximate and spaced from the container;
   an aerosol tube positioned around a portion of the acoustic transmitter pipe;
   an acoustic energy source being operatively coupled to the container for nebulization of the liquid and being configured for transmission of acoustic energy to a focal region of the liquid proximate said one end of the acoustic transmitter pipe whereby said liquid is forced toward an opposite end of the acoustic transmitter pipe and nebulized within the aerosol tube;
   wherein said energy source and said acoustic transmitter pipe are configured such that a guided spout of said liquid to be nebulized is emitted from said opposite end of said acoustic transmitter pipe; and
   wherein said guided spout is emitted with a diameter equal to a diameter of said opposite end of said acoustic transmitter pipe.

2. The nebulizer of claim 1 wherein the energy source is positioned below the container.

3. The nebulizer of claim 1 wherein the acoustic transmitter pipe is positioned so that said one end is proximate the bottom of the container.

4. The nebulizer of claim 1 wherein an internal diameter of the aerosol tube is greater than an outer diameter of the acoustic transmitter pipe at the opposite end of the acoustic transmitter pipe.

5. The nebulizer of claim 1 wherein the aerosol tube is positioned so that it is substantially coaxial with the acoustic transmitter pipe.

6. The nebulizer of claim 5 wherein the aerosol tube is connected to the opposite end of the acoustic transmitter pipe.

7. The nebulizer of claim 6 wherein the energy source vibrates the liquid proximate the opposite end of the acoustic transmitter pipe.

8. The nebulizer of claim 1 wherein the aerosol tube opens at its upper end into an expansion chamber which in turn communicates with an outlet duct.

9. The nebulizer of claim 8 wherein the expansion chamber is adapted to return non-nebulized liquid to the container via a drainage pipe.

10. The nebulizer of 8 further comprising a partition wall located to one side of the expansion chamber to separate the outlet duct from the acoustic transmitter pipe.

11. The nebulizer of claim 1 wherein the energy source comprises an ultrasonic transducer.

12. The nebulizer of claim 11 wherein the ultrasonic transducer has a concave shaped surface.

13. The nebulizer of claim 11 wherein the ultrasonic transducer is a bowl-shaped ultrasonic transducer.

14. The nebulizer of claim 1 wherein an internal diameter of the acoustic transmitter pipe is substantially equal to a diameter of the focal region.

15. The nebulizer of claim 1 wherein the acoustic transmitter pipe has a higher acoustic impedance than the liquid.

16. The nebulizer of claim 1 also comprising an air inlet for replenishment of air during nebulization of the liquid.

17. A nebulizer comprising:
   a reservoir for containing an initial volume of a liquid to be nebulized, said initial volume of said liquid having a liquid surface located at an initial surface level within said reservoir;
   a tubular sound-transmitting conduit for said liquid, said conduit having a liquid inlet end positioned within said reservoir at a liquid inlet location below said initial surface level, and a liquid outlet end positioned at a nebulizing location above said initial surface level;
   a source of ultrasonic energy configured to transmit said ultrasonic energy to a focal region located generally on an axis of said conduit adjacent to said inlet end of said conduit;
   said conduit being configured to contain a column of liquid extending from said liquid inlet end to said liquid outlet end and to transmit said ultrasonic energy from said focal region to said liquid outlet end, at least through said column of liquid, and
   said source of ultrasonic energy being operative to supply said ultrasonic energy to said focal region with sufficient intensity to advance said liquid to be nebulized through said conduit and out said liquid outlet end and to nebulize said liquid exiting from said outlet end;
   wherein said source of ultrasonic energy and conduit are configured such that a guided spout of said liquid to be nebulized is emitted from said liquid outlet end of said conduit; and wherein said guided spout is emitted with a diameter equal to a diameter of said liquid outlet end of said conduit.

18. The nebulizer of claim 17 wherein said reservoir has an interior bottom surface and said focal region is adjacent said interior bottom surface.

19. The nebulizer of claim 17 wherein said source of ultrasonic energy is a concave transducer.

20. The nebulizer of claim 17 wherein said conduit has a wall configured to transmit said ultrasonic energy from said liquid inlet end to said liquid outlet end.

21. The nebulizer of claim 17 wherein said ultrasonic energy is directed generally upward along said axis of said conduit.

* * * * *